United States Patent [19]

Malloy et al.

[11] Patent Number: 5,413,917
[45] Date of Patent: May 9, 1995

[54] METHOD OF DETERMINING SOURCES OF ACETYL-COA UNDER NONSTEADY-STATE CONDITIONS

[75] Inventors: Craig R. Malloy; F. Mark H. Jeffrey; A. Dean Sherry, all of Dallas, Tex.

[73] Assignee: Board of Regents, The University of Texas System, Austin, Tex.

[21] Appl. No.: 555,270

[22] Filed: Jul. 18, 1990

[51] Int. Cl.⁶ .................... C12Q 1/00; C12Q 1/02; C12Q 1/04

[52] U.S. Cl. .................................... 435/35; 435/4; 435/14; 435/29; 435/30; 436/56; 436/57; 436/63; 436/173; 424/9.3; 424/9.35

[58] Field of Search ............... 435/4, 35, 14, 30, 29; 424/1.1, 9; 436/173, 56, 57, 63

[56] References Cited

PUBLICATIONS

Cerdan J. Biol. Chem. v. 265 n. 22 pp. 12916–12926 (1990).

Behr et al Magnetic Resonance in Medicine 3 pp. 911–920 1986.

Williamson, J. R. and Krebs, H. A., Biochem. J. vol. 80, "Acetoacetate as Fuel of Respiration in the Prefused Rat Heart" pp. 540–547 (1961).

Williamson, J. R., Biochem. J. vol. 83, "Effects of Insulin and Diet on the Metabolism of L(+)-Lactate and Glucose by the Perfused Rat Heart" pp. 377–383 (1962).

Neely et al., Biochem. J. vol. 128, "The Effects of Increased Heart Work on the Tricarboxylate Cycle and its Interactions with Glycolysis in the Perfused Rat Heart", pp. 147–159 (1972).

Mickle et al., Cardiovascular Research vol. 20, "Exogenous Substrate Preference of the Post-Ischaemic Myocardium" pp. 256–263 (1986).

Myears et al., American Physiological Society, "Substrate Use in Ischemic and Reperfused Canine Myocardium: Quantitative Considerations" pp. H107–H114 (1987).

Liedtke et al., Circulation Research vol. 62, No. 3, "Changes in Substrate Metabolism and Effects of Excess Fatty Acids in Reperfused Myocardium" pp. 535–542 (Mar. 1988).

Wyns et al., Circulation Research vol. 65, No. 6, "Effects of Inhibition of Fatty Acid Oxidation on Myocardial Kinetics of $^{11}$C-Labeled Palmitate" pp. 1787–1797 (Dec. 1989).

Keijo J. Peuhkurinen, J. Mol. Cell. Cardiol. vol. 16, "Regulation of the Tricarboxylic Acid Cycle Pool Size in Heart Muscle" pp. 487–495 (1984).

H. L. Kornberg, Essays in Biochem. vol. 2, "Anaplerotic Sequences and their Role in Metabolism" pp. 1–31 (1966).

Chatzidakis, C. and Otto, David A., LIPIDS, vol. 22, No. 9, "Labeled Oxidation Products from [1-$^{14}$C], [U-$^{14}$C] and [16-$^{14}$C] Palmitate in Hepatocytes and Mitochondria" pp. 620–627 (1987).

Veerkamp et al., Biochemical Medicine and Metabolic Biology vol. 35, "$^{14}$CO$_2$ Production Is No Adequate Measure of [$^{14}$C] Fatty Acid Oxidation" pp. 248–259 (1986).

Lerch et al., Circulation vol. 64, No. 4, "Localization of Viable, Ischemic Myocardium by Positron-emission Tomography with $^{11}$C-Palmitate" pp. 689–699 (Oct. 1981).

(List continued on next page.)

*Primary Examiner*—Michael G. Wityshyn
*Assistant Examiner*—Jane A. Williams
*Attorney, Agent, or Firm*—Arnold White & Durkee

[57] ABSTRACT

The present invention relates to a method of measuring the contribution of one or more exogenously administered $^{13}$C-labeled substrates to acetyl-CoA. The measurement can be made in a tissue or cell using $^{13}$C NMR without the constraint of metabolic or isotopic steady-state. Furthermore, the method permits the determination even when spectral lines are broad due to B$_0$ inhomogeneity, thereby opening the way for substrate utilization studies in vivo. The method does not require many of the simplifying assumptions involved in $^{11}$C or $^{14}$C methods, and, since a stable isotope, $^{13}$C, is used a wide variety of compounds with complex labeling patterns may be synthesized and studied.

30 Claims, 7 Drawing Sheets

OTHER PUBLICATIONS

Schwaiger et al., JACC vol. 6, No. 2, "Sustained Regional Abnormalities in Cardiac Metabolism After Transient Ischemia in the Chronic Dog Model" pp. 336–347 (Aug. 1985).

Brown et al., Circulation vol. 76, No. 3, "Delineation of Myocardial Oxygen Utilization With Carbon–11–Labeled Acetate" pp. 687–696 (Sep. 1987).

London, Robert E. Prog. in NMR Spectroscopy, vol. 20, "$^{13}$C Labeling in Metabolic Regulation Studies" pp. 337–383 (1988).

Walker et al., J. of Biolog. Chem. vol. 257, No. 3, "$^{13}$C Nuclear Magnetic Resonance Studies of the Biosynthesis by *Microbacterium ammoniaphilum* of L-Glutamate Selectively Enriched with Carbon–13" pp. 1189–1195, Feb. 10, 1982.

Chance et al., The J. of Biolog. Chem. vol. 258, No. 22 "Mathematical Analysis of Isotope Labeling in the Citric Acid Cycle with Applications to $^{13}$C NMR Studies in Perfused Rat Hearts" pp. 13785–13794 (Nov. 25, 1983).

Sheila M. Cohen, The J. of Biolog. Chem. vol. 258 No. 23, "Simultaneous $^{13}$C and $^{31}$P NMR Studies of Perfused Rat Liver" pp. 14294–14308 (Dec. 10, 1983).

Walker, T. E. and London, R. E., Applied and Environmental Microbiology, vol. 53, No. 1, "Biosynthetic Preparation of L-[$^{13}$C]- and [$^{15}$N]Glutamate by *Brevibacterium flavum*" pp. 92–98 (Jan. 1987).

Malloy et al., J of Biolog Chem vol. 263 No. 15 "Evaluation of Carbon Flux and Substrate Selection Through Alternate Pathways Involving the Citric Acid Cycle of the Heart by $^{13}$C NMR Spectroscopy" pp. 6964–6971 (May 25, 1988).

Sherry et al., Biochem. J. vol. 254, "Propionate metabolism in the rat heart by $^{13}$C n.m.r. spectroscopy" pp. 593–598 (1988).

Craig R. Malloy in Structural and Organizational Aspects of Metabolic Regulation, "Analysis of Substrate Utilization by $^{13}$C NMR Spectroscopy" (Alan R. Liss, Inc., 1990, pp. 363–374).

Moreleand, C. G. and Carroll, F. I., J. of Magnetic Resonance vol. 15, "$^{13}$C–$^{13}$C Dipolar Interactions as a Relaxation Mechanism" pp. 596–599 (1974).

LeCocq, C. and Lallemand, J–Y, J.C.S. Chem. Comm., "Precise Carbon–13 N.M.R. Multiplicity Determination" pp. 150–152 (1981).

Patt, S. L. and Shoolery, J. N., J. or Magnetic Resonance vol. 46, "Attached Proton Test for Carbon–13 NMR", pp. 535–539 (1982).

Malloy et al., FEBS Letters, vol. 212, No. 1, "Carbon flux through citric acid cycle pathways in perfused heart by $^{13}$C NMR spectroscopy" pp. 58–62 (Feb. 1987).

Sheila M. Cohen, Biochemistry vol. 26, No. 2, "Effects of Insulin on Perfused Liver from Streptozotocin–Diabetic and Untreated Rates: $^{13}$C NMR Assay of Pyruvate Kinase Flux" pp. 573–580 (1987).

Sheila M. Cohen, Biochemistry vol. 26, No. 2, "$^{13}$C NMR Study of Effects of Fasting and Diabetes on the Metabolism of Pyruvate in the Tricarboxylic Acid Cycle and of the Utilization of Pyruvate and Ethanol in Lipogenesis in Perfused Rat Liver" pp. 581–589 (1987).

METHOD OF DETERMINING SOURCES OF ACETYL-COA UNDER NONSTEADY-STATE CONDITIONS

The United States Government may have certain rights in the present invention pursuant to the terms of Grant No. HL 34557 awarded by the National Institutes of Health and a Merit Review and Career Development award from the Department of Veteran's Affairs.

BACKGROUND OF THE INVENTION

1. Field of the Invention

The invention relates to the use of nuclear magnetic resonance spectroscopy (NMR) to measure the utilization of one or more substrates in cells and tissues. In particular aspects the invention concerns the selection and use of $^{13}C$-enriched substrate(s) which are ultimately metabolized to acetyl-CoA. This method concerns the analysis of a single NMR spectrum which may be acquired at a time when steady-state isotopic or metabolic conditions may not have been established. The information obtained from this analysis is the fraction of acetyl CoA derived from the $^{13}C$-enriched substrate or substrates, and from unlabeled sources.

2. Description of Related Art

The relative rates of utilization of various exogenous and/or endogenous substrates in normal cells and tissues may be sensitive to many factors including cellular work rate, physiologic state, drugs, toxins, hormones, and the like. Substrate utilization may also be sensitive to disease states such as ischemia, infection, inflammation, trauma, congenital defects in metabolism, acquired defects in metabolism, or during malignant transformations such as cancer. Thus, precise quantitation of substrate utilization could have broad application since it may provide insight into the integrated functional state and viability of cells or a tissue.

Acetyl Coenzyme A (acetyl-CoA) is a key intermediate in cellular biochemistry. It is oxidized in the citric acid cycle for the production of energy, and it is a precursor in multiple biosynthetic processes. Acetyl-CoA may be derived from numerous compounds, each of which must be metabolized through different pathways subject to complex and interacting regulatory processes. Thus, the relative contribution of one or more substrates to acetyl-CoA reflects cellular metabolic state. Since this measurement is so important for the understanding of tissue metabolism, it has been the objective of numerous studies in many cellular preparations and tissues (see references 1-7 for examples using heart tissue).

The measurement of the contribution of a compound to acetyl-CoA ordinarily requires an estimate of the rate of acetyl-CoA utilization, typically from oxygen consumption, and the rate of substrate utilization under steady-state conditions. The latter usually is measured by the rate of appearance of $^{14}CO_2$ from a $^{14}C$-enriched substrate, the rate of removal of substrate from the perfusion medium, or multiexponential analysis of $^{11}C$ time-activity curves in tissues utilizing $^{11}C$-enriched substrates.

However, substrate and oxygen removal are difficult to measure under some important conditions, and metabolic and isotopic steady-state often cannot be assured. Further, since pyruvate may be metabolized by either pyruvate dehydrogenase or through a pyruvate carboxylation pathway the appearance of $^{14}CO_2$ from $^{14}C$-enriched pyruvate (or its precursors) indicates net substrate oxidation only if the carbon skeleton enters the citric acid cycle via pyruvate dehydrogenase (8,9) Similarly $^{14}CO_2$ release from fatty acids is an unreliable measure of this oxidation (10,11). Thus, standard methods for assessing substrate competition and oxidation are often not satisfactory for rapidly changing or spatially heterogeneous metabolic states, or if more than one pathway is available for carbon flow into the citric acid cycle.

In spite of these limitations on traditional methods, there is substantial interest in the measurement of substrate oxidation for the assessment of tissue metabolism and viability. For example, position emission tomography (PET) has been used to examine regional myocardial metabolism during ischemic and other states. However, the interpretation of some PET observations is controversial, for example, fatty acid oxidation in ischemic reperfused myocardium. PET studies generally have concluded that fatty acid oxidation is suppressed, but other reports have not validated this finding (4–7,12,13). PET is fundamentally limited by the lack of knowledge of the chemical state of the tracer. For example, a compound may enter a cell where it may be trapped and stored, metabolized to acetyl-CoA and oxidized, or it may remain in the cell briefly and then diffuse out, unchanged. Numerous assumptions regarding the metabolic fate of a tracer are therefore required.

For these reasons, some recent PET studies have emphasized the utilization of a very simple compound, acetate, which is not subject to many of the complex physiological processes which regulate normal metabolism (14). Analysis of the results is thereby simplified, but acetate is not a physiological substrate. Biochemical and physiological studies using $^{11}C$ are also limited by the problem of working with a radioactive element with a very short half-life. Thus, a nearby cyclotron is essential, and rapid chemical synthesis is required. The study of some molecules or certain labeling patterns is simply not practical.

The analogous use of $^{13}C$ enriched substrates to monitor intermediary metabolism has been established (15). Multiple enriched intermediates of the citric acid cycle may be detected by NMR spectroscopy (15-19). It has been shown that citric acid cycle flux may be determined if the fractional enrichments in intermediates are measured repeatedly after the addition of enriched substrate (17). This method, however, assumes steady-state flux conditions, constant intermediate pool sizes, and good temporal resolution. Although collection of in vivo data is theoretically possible, the method depends on measurement of fractional enrichment in glutamate and other intermediates, a requirement which may be difficult to meet under many important conditions.

An alternative to the measurement of absolute citric acid cycle flux is the measurement of the relative rates of competing pathways feeding acetyl-CoA. This approach has been reported previously. In some instances, metabolic and isotopic steady-state were assumed for the purposes of data analysis and these conditions were established experimentally (20,21). Other reports indicated that insight into the pathways feeding acetyl-CoA could be obtained by $^{13}C$ NMR spectroscopy (18,19). Finally, one report described how to measure the ratio of the contribution of two labeled substrates to acetyl-CoA under nonsteady-state conditions (22). This method is limited, however, in that it requires that two different labeled substrates be administered, and the fraction of acetyl-CoA derived from unlabeled sources is not determined. Thus, methods for the measurement of the fraction of acetyl-CoA derived from a particular substrate or substrates under nonsteady state conditions have not been reported.

$^{13}C$ NMR is useful for the monitoring of metabolism of $^{13}C$ labeled compounds in experimental animals and humans. However, there are three important factors limiting study of substrate utilization in vivo. First, there is the consideration of expense. Significant amounts of relatively expensive labeled compounds make it difficult to maintain a constant concentration in the blood for the time required to attain isotopic steadystate. Second, many conditions of interest may involve rapidly changing metabolic conditions, and metabolic state cannot be assumed. Finally, an isotopomer analysis applicable in vivo to determine $^{13}C$ contributions to the carbon skeleton of citric acid cycle components has been applied only when $B_0$ homogeneity was sufficient to allow resolution of $^{13}C$—$^{13}C$ scalar coupling. This condition of homogeneity is unlikely to be the case under the circumstances of many in vivo measurements.

The present invention addresses the problem of non-steady-state conditions and field homogeneity requirements. It is shown that the contribution of one or more exogenously administered $^{13}C$-labeled substrates to acetyl CoA can be determined in a tissue or cell using $^{13}C$ NMR without the constraint of metabolic or isotopic steady-state. Furthermore, the method permits the determination even when spectral lines are broad due to $B_0$ inhomogeneity, thereby opening the way for substrate utilization studies in vivo. The method does not require many of the simplifying assumptions involved in $^{11}C$ or $^{14}C$ methods, and, since a stable isotope, $^{13}C$, is used, a wide variety of compounds with complex labeling patterns may be synthesized and studied.

SUMMARY OF THE INVENTION

The present invention relates to a method of measuring the sources of acetyl-CoA in a tissue or cell metabolizing carbon labeled compounds by determining the enrichment patterns in the skeleton of selected metabolic products. Steady-state metabolic and isotopic conditions need not apply. The method may be practiced using a $^{13}C$ NMR method requiring a single spectrum, and up to three different $^{13}C$ labeled substrates may be studied simultaneously.

The invention, in a general sense, involves preparing at least one labeled carbon compound having carbons which are capable of entering the citric acid cycle, administering the compound in vitro or in vivo to cells or a tissue having citric acid cycle capacity, and then measuring the enrichment pattern in a citric acid cycle component or in the carbons of a compound that exchange with the citric acid cycle. The method is rapid and convenient and may be quite useful for in vivo measurements because it does not require that metabolic steady-state be achieved. It is also novel in that measurements can be made prior to achievement of steady-state isotopic carbon distribution. In a practical sense, measurements may often be made as early as a few minutes after a labeled substrate is supplied to the cell or tissue.

The $^{13}C$ labeling pattern in the substrate is selected by the operator after considering the labeling pattern in acetyl CoA after the substrate is metabolized through known biochemical pathways. The following table illustrates the flexibility of the method and shows the expected labeling pattern in acetyl CoA depending on the number of substrates to be investigated.

TABLE 1

| Number of Labeled Substrates | Labeling Pattern in Acetyl-CoA | Example of Labeled Substrate |
|---|---|---|
| 1 | [2-$^{13}C$] acetyl-CoA or [1,2-$^{13}C$] acetyl-CoA | [3-$^{13}C$] pyruvate or [2,3-$^{13}C$] pyruvate |
| 2 | [2-$^{13}C$] acetyl-CoA and [1,2-$^{13}C$] acetyl-CoA or [1,2-$^{13}C$] acetyl-CoA and [1-$^{13}C$] acetyl-CoA or [2-$^{13}C$] acetyl-CoA and [1-$^{13}C$] acetyl-CoA | [3-$^{13}C$] pyruvate and [U-$^{13}C$] glucose [2,3-$^{13}C$] pyruvate and [1-$^{13}C$] acetate [3-$^{13}C$] pyruvate and [1-$^{13}C$] acetate |
| 3 | [1-$^{13}C$] acetyl-CoA and [1,2-$^{13}C$] acetyl-CoA and [2-$^{13}C$] acetyl-CoA | [2-$^{13}C$] pyruvate and [U-$^{13}C$] fatty acid and [1-$^{13}C$] glucose |

Examples of suitable substrates include acetate, lactate, pyruvate, glucose and other sugars, alanine and other amino acids, ethanol, acetoacetate and other ketone bodies, and short, medium or long chain fatty acids. Alternatively, the labeled carbon may enter the citric acid cycle through intermediates other than acetyl CoA such as the case of propionate oxidation, an anaplerotic reaction (9,21). However, it is essential that the labeled carbon eventually reach acetyl-CoA in order that the C4 and/or C5 of citrate become enriched. A third group of labeled compounds may already be members of the citric acid cycle such as citrate, isocitrate, cis-aconitate or α-ketoglutarate. In this case the method enables the effective contribution of that compound to acetyl-CoA.

Substrate utilization is determined in a cell or tissue which has an active citric acid cycle capacity. Some tissues, of course, such as red cells do not have citric acid cycle activity but are capable of metabolizing compounds to precursors which can enter the cycle of other tissues. Therefore, in an in vivo situation a $^{13}C$-labeled compound, for example, can be partially metabolized by components in the red cells or other tissues and later utilized in a tissue of interest where substrate utilization is to be determined.

After the labeled compound has been administered, the enrichment pattern in one or more products is measured. The measurement is performed on a compound within the citric acid cycle or on a compound that can exchange carbon atoms into the citric acid cycle. The compound which is used for the determination of labeling patterns must preserve the distribution of carbon label in C3, C4 and C5 of α-ketoglutarate. In many cases, the most convenient compound for making labeled carbon measurements is glutamate. Glutamate is in rapid equilibrium with α-ketoglutarate of citric acid cycle. However, in practice, any equivalent component of the citric acid cycle could be used, including derivatives of citrate, isocitrate, cis-aconitate, ketoglutarate, glutamine, γ-aminobutyric acid, and the like.

An important aspect of this general method of measuring substrate utilization is that a single spectrum can be made before steady-state metabolic or isotopic steady-state has been achieved. Furthermore, the measurement need be made only on a single tissue sample so that in human patients there is decreased stress from not having to obtain multiple tissue samples. Also, since measurement is made shortly after the administration of labeled substrate, there is no need for infusion or perfusion of large quantities of substrate. This may make a significant difference in cost.

It will be appreciated that this method of determining substrate utilization can be used both in vivo and in vitro. In vivo determinations would involve obtaining a tissue sample or biopsy such as from heart, brain, liver, skeletal muscle, lung, pancreas, lymphoid tissue, white cells, bone marrow or kidney after a suitable period of time, and then making a $^{13}C$ measurement. Substrate utilization determinations may also be made on single cells, either prokaryotes or eukaryotes. Particular examples include yeast or bacterial cells.

Measurements are preferably made using nuclear magnetic resonance. This is a powerful technique and at present would be the method of choice for determining isotope distribution. Mass spectrometry could also be used to measure patterns of $^{13}C$ enrichment in selected molecules. It should also be appreciated that other types of isotopes might be used in place of $^{13}C$ and that these isotopes, for example $^{14}C$, could be detected by other than NMR methods. It will be appreciated that as long as the distribution in the skeleton is preserved in the citric acid cycle, other carbon labels will work in this analysis, provided patterns of enrichment can be determined.

$^{13}C$ NMR measurements will typically be made by determining total resonance areas attributed to the different carbon atoms of the molecules selected for measurements and the multiplets within each resonance. Appropriate corrections for nuclear Overhauser effects and $^{13}C$—$^{13}C$ interactions which affect $T_1$ may be required.

Utilization of a single $^{13}C$-labeled substrate is determined using resonance areas of a multiplet of carbon C4 and a resonance area ratio of carbons C4 and C3 as shown in example 2 and in FIGS. 4 and 5.

Substrate utilization of two $^{13}C$-labeled compounds may also be determined using this method. This entails measuring $^{13}C$ NMR resonance areas of two multiplets of carbon C4 and resonance area ratios of carbon C3 to C4. Under some conditions the ratio of C5 to C4 must be measured.

Substrate utilization for three administered $^{13}C$-labeled compounds can also be determined. This involves measuring $^{13}C$ NMR resonance areas of two multiplets of carbon C4 and a resonance area ratios of carbon C3 to C4 and C5 to C4.

Position of $^{13}C$-labeling in the administered compound will determine the position of the $^{13}C$ in the skeleton of the compound which is a component of the citric acid cycle. All compounds entering the citric acid cycle through acetyl-CoA will show labels in the skeletal 3 and 4 positions of components of the citric acid cycle when the acetyl-CoA is labeled in the number 2 position of the acetate group. If the acetyl carbon 1 position is labeled with $^{13}C$, an enrichment in the C5 position of the skeletal components of the citric acid cycle will be observed. When the carbon C5 position is enriched $^{13}C$ NMR measurements will include measuring multiplets in the $^{13}C$ NMR resonance of the C5 carbon. It may be necessary to make corrections for the effects of $^{13}C$—$^{13}C$ dipolar interactions on $T_1$ and nuclear Overhauser effects under these conditions. These methods of correction are standard and are well known to those skilled in the art (23).

In vivo determinations of substrate utilization are also an important aspect of this method. One potential use is the assessment of brain metabolic state. In making this assessment, $^{13}C$-labeled glucose would be supplied to the brain. This could be done in a variety of ways, including appropriate administration of the $^{13}C$-labeled glucose as by intravenous injection. A $^{13}C$ NMR measurement would be performed on the brain after the tissue had been exposed to the $^{13}C$-labeled glucose. The time of exposure would depend on the nature of the determination and conditions, but would generally be performed shortly after administering the $^{13}C$-labeled glucose. It is one of the unique aspects of this invention that measurement may be made before metabolic or isotopic steady-state is attained.

Another important use of this method is the in vivo determination of regional variations in substrate utilization of ischemic tissue. This involves the steps of administering a $^{13}C$-labeled compound and then performing a $^{13}C$ NMR measurement on the tissue sample after the tissue has been exposed to the compound. The measurement may be performed before metabolic and isotopomeric steady-state has been achieved. Regional substrate utilization can be determined, a method which would be particularly useful in determining tissue damage after heart attacks in experimental animals or human patients.

Many other examples of in vivo applications using the method of the present invention can be envisioned. These include metabolism in biopsied tissue, integration with NMR imaging methods, imaging substrate utilization, analysis of consequences of genetic engineering and cellular identification through metabolic fingerprinting.

In determining metabolism in biopsied tissues, one to three $^{13}C$-enriched substrates could be infused into an animal or human for diagnostic purposes. The tissue of interest such as an abnormal mass could be biopsied surgically using standard procedures, or studied directly by in vivo NMR. The biopsied sample would be extracted using standard methods, studied by NMR or other techniques and analyzed using the described method.

Those skilled in the art are familiar with methods which allow the accumulation of high resolution spectra from regions of tissue selected by standard magnetic resonance imaging. Direct extension of these methods will allow measurement of metabolism in tissues selected from magnetic resonance images, and the information obtained from this metabolic analysis will improve the sensitivity and specificity of the integrated examination.

Construction of images based on spatially resolved spectroscopic data is also well known to those skilled in the art. For example, current methods allow the acquisition of $^{31}P$ NMR spectra from multiple volumes in the human brain, heart and other organs. These spectra may be presented as images of information selectively derived from the $^{31}P$ NMR spectrum, such as an image of phosphocreatine concentration. Similarly, the acquisition of the spectra described herein and application of the analysis would allow construction of quantitative images of substrate utilization in animals and humans.

The genome of a cell line or tissue may be modified using current methods of genetic engineering. These modifications may have specific and anticipated consequences (for example, reduced activity of an enzyme) or extensive and unexpected consequences for intermediary metabolism. This method would provide a very simple and convenient technique to prove that the expected effects of genetic engineering have occurred, to investigate the overall consequences for cellular metabolism, or to look for unanticipated consequences of the intervention.

Metabolic fingerprinting could be developed using the method of the present invention. Cell lines or cultures of prokaryotes such as bacteria or eukaryotes such as yeast or tumor cells have variable requirements for exogenous substrate. The patterns of substrate utilization when multiple substrates are available may be characteristic of a particular cell line. It would be quite simple to provide one to three labeled compounds to the cells. The compounds can be judiciously selected to probe specific pathways, for example, transamination, activity of pyruvate dehydrogenase, activity of beta oxidation, activity of glycolysis and similar activities. NMR obtained in vivo or from tissue extracts could then be subjected to the analysis of the present invention.

DETAILED DESCRIPTION OF PREFERRED EMBODIMENTS

An important aspect of the invention is its application to samples in which steady-state metabolic or isotopic conditions have not been attained. The method determines the sources of acetyl-CoA and assumes only that acetyl-CoA has become enriched in carbon from a carbon-labeled substrate.

Figure 1:
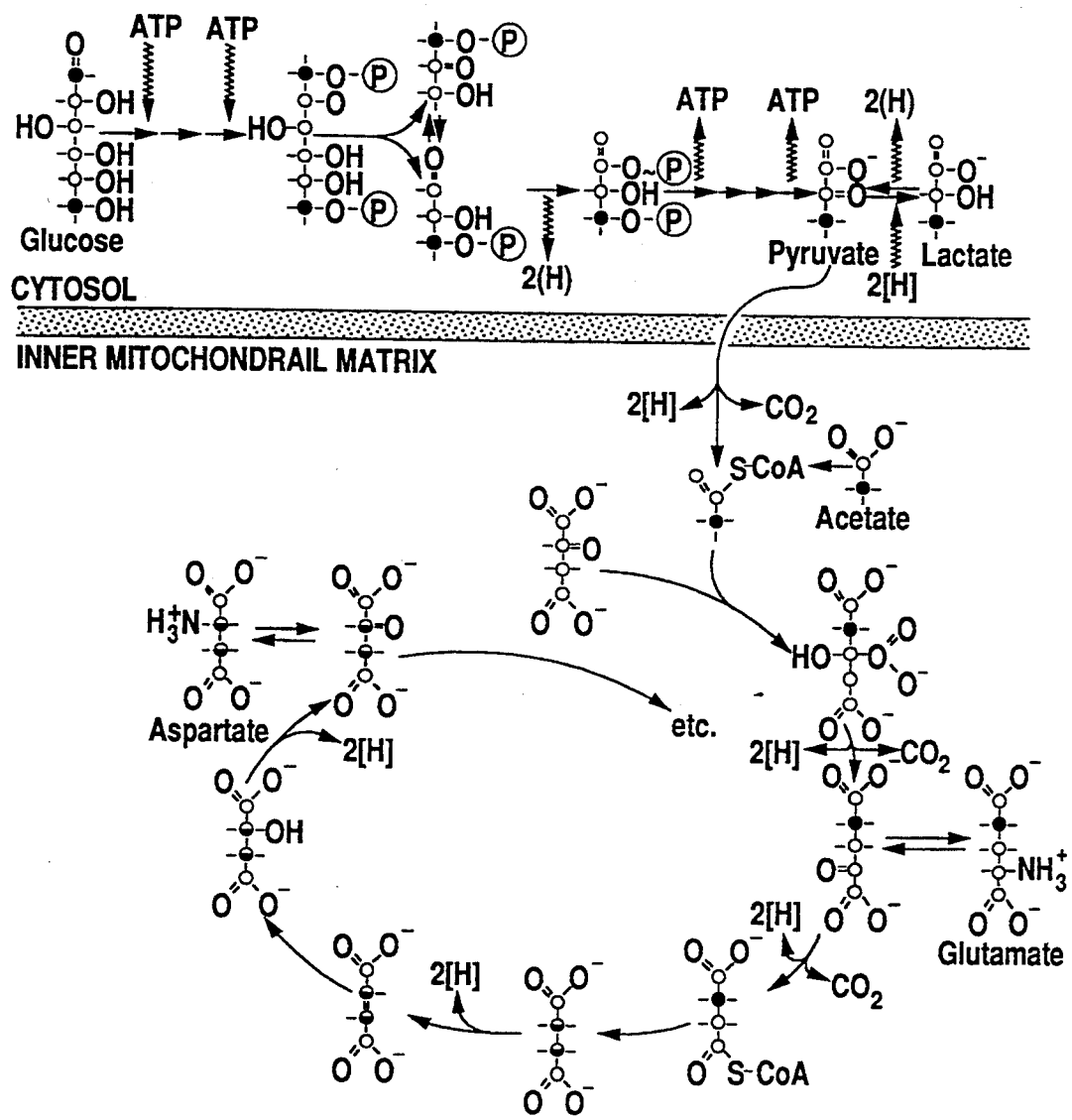
FIG. 1 is a diagram showing citric acid components and some of the components feeding into the cycle. The half-filled circles indicate scrambling in fumarate and succinate. Many different compounds could yield [2-$^{13}$C] acetyl-CoA.

It is an assumption of the method that oxaloacetate has become enriched in $^{13}$C. The only oxaloacetate carbon position relevant to the nonsteady-state analysis is the carbonyl carbon, C2, since this carbon becomes C3 of glutamate after ½ turn of the citric acid cycle. C4 and C3 of oxaloacetate become, respectively, C1 and C2 of glutamate and are not involved in this analysis. C1 of oxaloacetate is lost as $CO_2$ at the isocitrate dehydrogenase step, as indicated in FIG. 1. Because relative enrichments in the acetyl-CoA pool are being examined, the absolute enrichment in the C2 of oxaloacetate need not be known.

The theory of this method will be presented for moderately complex conditions which produce three acetyl-CoA isotopomers, for example, the use of [U-$^{13}$C] glucose and [3-$^{13}$C] lactate. More complex conditions are described below. The simplicity of the technique is demonstrated in FIG. 2. The chance that an oxaloacetate molecule labeled in the 2 carbon will condense with a given acetyl-CoA isotopomer equals the relative concentration of that isotopomer in the acetyl-CoA pool. Three different acetyl-CoA isotopomers may occur under these illustrative conditions: unlabeled acetyl-CoA from unlabeled sources, [2-$^{13}$C] acetyl-CoA from lactate, and [1,2-$^{13}$C] acetyl-CoA from glucose. Their relative concentrations are defined as $F_{c0}$, $F_{c2}$ and $F_{c3}$, respectively. Although glutamate has 32 possible isotopomers, only 24 may occur under these conditions (since there is no pathway for generation of [1-$^{13}$C] acetyl-CoA). Variables which indicate the relative concentrations of glutamate isotopomers are:

$X_1 = [[1,2,3,4,5-^{12}C]$ glutamate]/[glutamate]
$X_2 = [[1^{13}C]$ glutamate]/[glutamate]
$X_3 = [[2-^{13}C]$ glutamate]/[glutamate]
$X_4 = [[1,2-^{13}C]$ glutamate]/[glutamate[
$X_5 = [[3-^{13}C]$ glutamate]/[glutamate]
$X_6 = [[1,3-^{13}c]$ glutamate]/[glutamate]
$X_7 = [[2,3-^{13}C]$ glutamate]/[glutamate]
$X_8 = [[1,2,3=^{13}C]$ glutamate]/[glutamate]

Similarly, $X_9$–$X_{16}$ are identical to the first group, except that carbon 4 (but not carbon 5) is enriched. Enrichment in carbon 5 but not carbon 4 is represented by $X_{17}$–$X_{24}$, which in this case are 0. Finally, $X_{25}$–$X_{32}$ refer to the same pattern of labeling in carbons 1, 2 and 3, plus labeling in both carbons 4 and 5. By definition, $F_{c0}+F_{c2}+F_{c3}=1$, and $X_1+X_2+\ldots+X_{32}=1$. Six groups of glutamate isotopomers may be defined as:

$W_1=X_1+X_2+X_3+X_4$ (not labeled in C3, C4 or C5)

$W_2=X_5+X_6+X_7+X_8$ (labeled in C3 but not C4 or C5)

$W_3=X_9+X_{10}+X_{11}+X_{12}$ (not labeled in C3 or C5, labeled in C4)

$W_4=X_{13}+X_{14}+X_{15}+X_{16}$ (labeled in C3 and C4, not labeled in C5)

$W_5=X_{25}+X_{26}+X_{27}+X_{28}$ (not labeled in C3, labeled in C4 and C5)

$W_6=X_{29}+X_{30}+X_{31}+X_{32}$ (labeled in C3, C4 and C5)

The area of the 4 carbon resonance relative to the 3 carbon resonance is defined as $C4/C3=(W_3+W_4+W_5+W_6)/(W_2+W_4+W_6)$. The area of the components of the 4 carbon multiplet are defined relative to the total area of the resonance (17): singlet, C4S; doublet due to $J_{34}$, $C4D34=W_4/(W_3+W_4+W_5+W_6)$; doublet due to J45, C4D45; doublet of doublets (quartet), $C4Q=W_6/(W_3+W_1+W_5+W_6)$.

Figure 2:
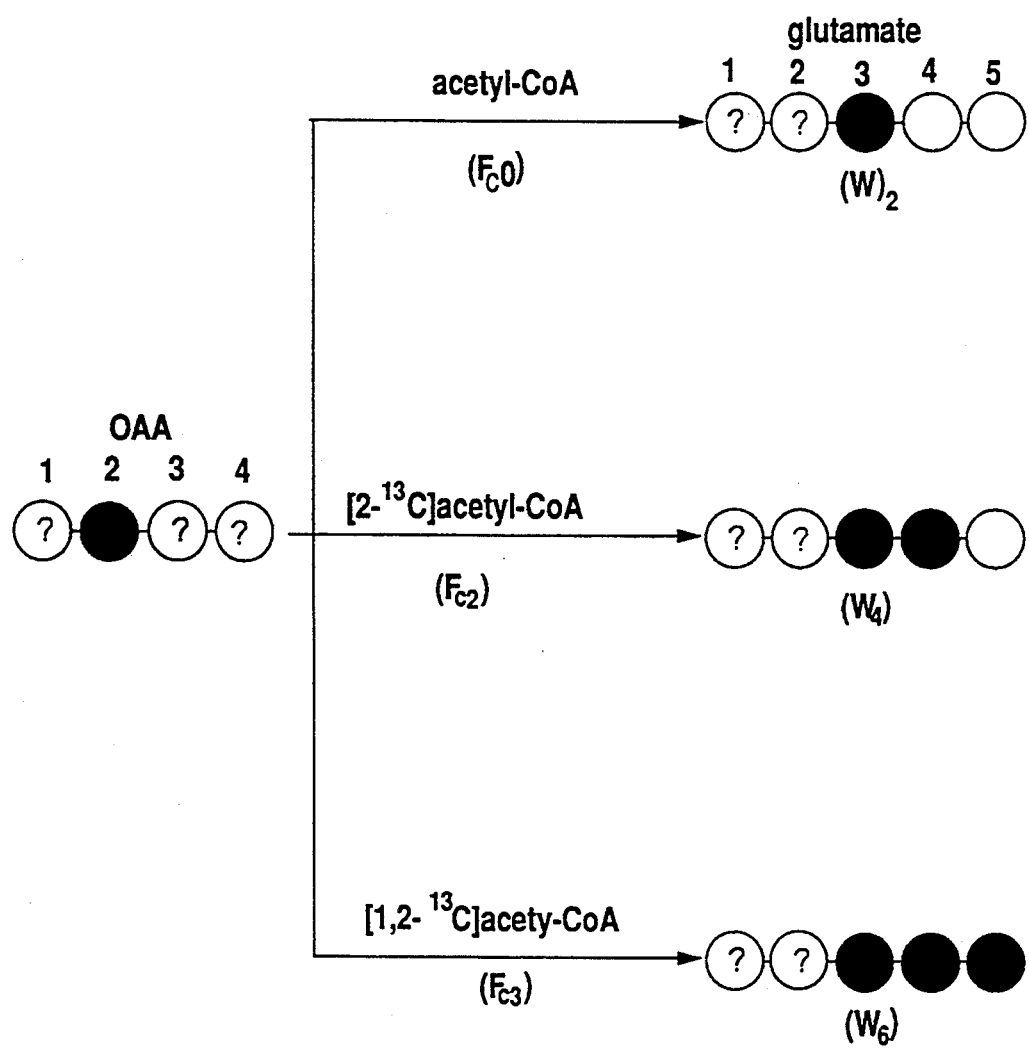
FIG. 2 presents the principles of the nonsteady-state analysis. OAA is oxaloacetate. The "w" variables refer to groups of isotopomers described in the specification. The filled circles indicate $^{13}$C the empty circles indicate $^{12}$C and the ? indicates carbons not relevant to the analysis. The "$f_c$" variables indicate the enrichment pattern of acetyl-CoA and are defined in the specification.

As illustrated in FIG. 2, $F_{c0}$, $F_{c2}$ and $F_{c3}$ are quantitatively related to $W_2$, $W_4$, and $W_6$, respectively. The chance that an oxaloacetate molecule labeled in C2 will condense with unlabeled acetyl-CoA equals $F_{c0}$. Therefore, $F_{c0}/(F_{c0}+F_{c2}+F_{c3})=W_2/(W_2+W_4+W_6)$. Similar relations may be derived for $F_{c2}$ and $F_{c3}$. By combining these relationships, one obtains quite simply, $(C4D34)(C4/C3)=W_4/(W_2+W_4+W_6)=F_{c0}/(F_{c0}+F_{c2}+F_{c3})=F_{c2}$  Equation [1]

$(C4Q)(C4/C3)=W_6/(W_2+W_4+W_6)=F_{c3}/(F_{c0}+F_{c2}+F_{c3})=F_{c3}$  Equation [2]

Therefore, by measuring two C4 multiplet components and the C4/C3 ratio, one can obtain values for $F_{c2}$, $F_{c3}$ and by difference, $F_{c0}$, under any nonsteady-state circumstances.

Figure 7:
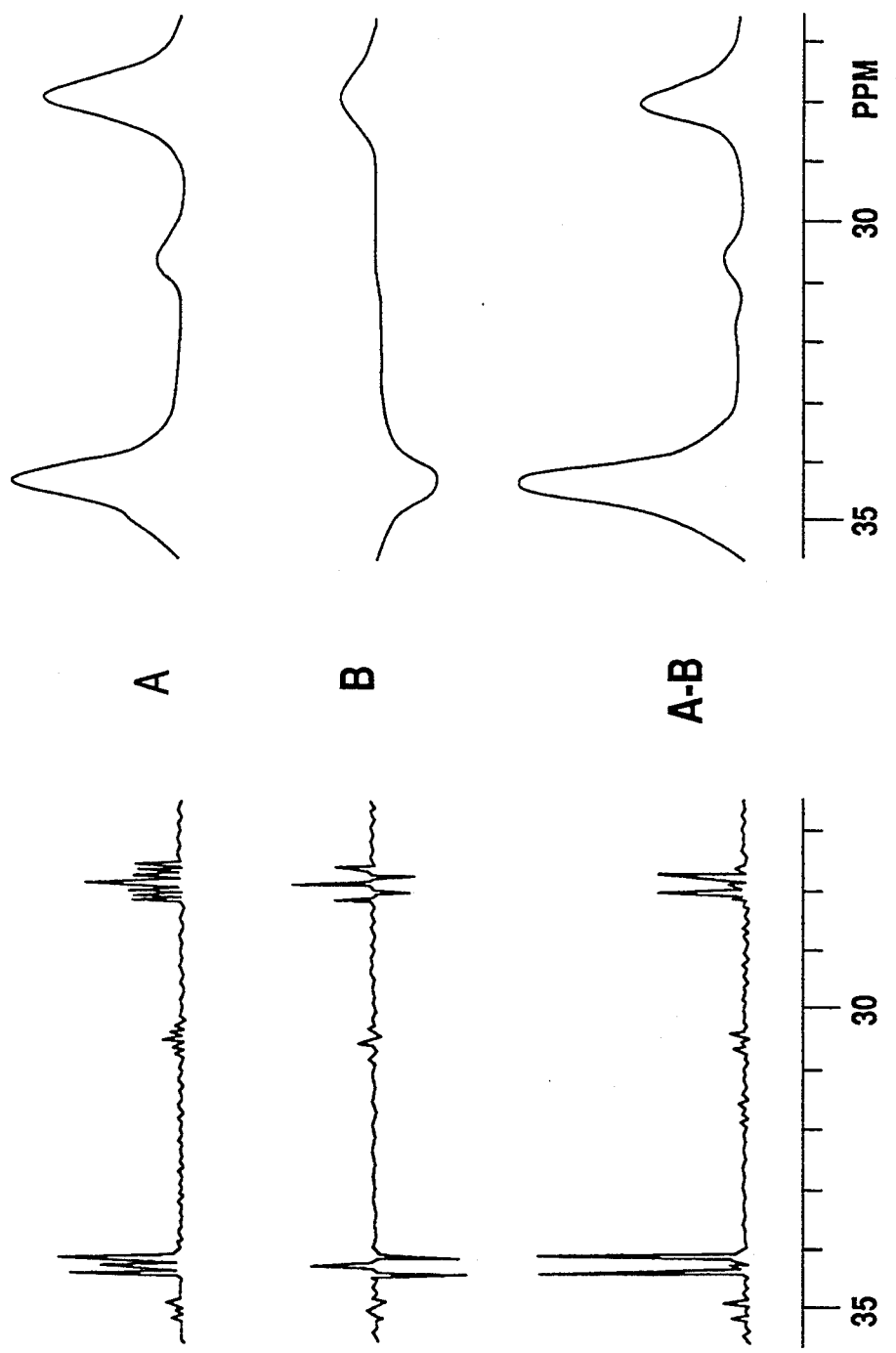
FIG. 7 shows proton-decoupled $^{13}$C NMR spectra acquired using J modulated spin echo. The difference between A (one pulse experiment) and B (spin echo) is shown as A-B. Good resolution (left side) and poor resolution (right side) spectra are shown for both sequences.

In practice, $B_0$ field homogeneity may not be adequate to resolve $^{13}$C—$^{13}$C coupling, however, under these circumstances, special pulse sequences may be employed. A J modulated spin echo may be used to select the phase of each multiplet in a resonance (24,25) since the evolution of a spin system under the influence of scalar coupling is not altered by $B_0$ inhomogeneity. The pulse sequence $90°$-$\tau$-$180°$-$\tau$ acquire (where $\tau=\frac{1}{4}J$) was used to create a 180° phase difference between the doublet ($J_{34}=34$ Hz) and the other lines in the C3 and C4 resonance under conditions producing well resolved or poorly resolved resonances. This is demonstrated in FIG. 7. As shown, two fully relaxed spectra may be accumulated (preferably over the same time period in separate regions of computer memory), using a single pulse and a second using the spin-echo sequence. The C4/C3 ratio is obtained from the first spectrum 7A and C4D34 is obtained from the difference between the two spectra, $(C4D34=(A-B)/2A=0.5-B/2A$, where A is the area of the C4 resonance after a standard scan and B is the area with a spin echo.)

This analysis may be extended to more complex substrate combinations and metabolic conditions. [1-$^{13}$C] acetyl-CoA may be generated from a labeled compound provided to the tissue such as [2-$^{13}$C] lactate, or by $^{13}$C flowing from oxaloacetate to phosphoenolpyruvate, pyruvate, and ultimately acetyl-CoA. Under either circumstance the resulting glutamate may become enriched in C5 but not C4. This analysis (equations 1 and 2) would remain valid, but the fraction of acetyl-CoA which is unlabeled (Fco) could not be distinguished from the fraction of acetyl-CoA enriched in C1 (defined as $F_{c1}$ in earlier studies (22)). The ratio $F_{c1}/F_{c3}$ may be determined directly from the multiplets in the $^{13}$C NMR resonance of the C5 of glutamate: $F_{c1}/F_{c3}=C5S/C5D$, where C5S and C5D refer to the areas of the singlet and doublet. However, appropriate experimental conditions or corrections must be used to quantify the $^{13}$C-enrichment in glutamate C5 because of the effects of $^{13}$C—$^{13}$C dipolar interaction on $T_1$ (15,16,23). Hence, the relative concentrations of all 4 acetyl-CoA isotopomers may be determined in a single experiment.

The following examples are intended to illustrate specific embodiments of the present invention, not to exhaustively describe all possible embodiments. Those skilled in this field will recognize that modifications could be made to the disclosed methods and that other applications would remain within the scope of the present invention.

EXAMPLES

NMR Methods

Proton decoupled $^{13}$C NMR spectra were obtained at 125.7 MHz with a GN 500 spectrometer. Tissue extract samples were studied in a dual $^1$H-$^{13}$C 5 mm probe under high resolution conditions using WALTZ decoupling, a 45° observe pulse, 16,384 data points, 8000 scans, and a pulse delay of 6 secs. Intact hearts were studied in an 18 mm tube using WALTZ decoupling, a 30° observe pulse, 16,384 data points, and a delay between pulses of 1.3 sec. In the intact heart experiments, field homogeneity was adjusted using the free induction decay of the $^{23}$Na signal; typical $^{23}$Na line widths were 17–22 Hz.

Heart Perfusions

Male Sprague-Dawley rats weighing 300–350 g were anesthetized in an ether atmosphere. Male New Zealand White rabbits weighing 2.5–3.0 kg were anesthetized using intramuscular acepromazine (0.7 mg/kg) and nembutal (24 μg/kg). Hearts were rapidly excised and placed briefly in 4° C.arrest medium. The aorta was immediately cannulated and perfused retrograde at a pressure of 70 cm $H_2O$. The perfusate, a modified, phosphate-free Krebs-Henseleit medium, was gassed with 95% $O_2$ - 5% $CO_2$ and contained: 119.2 mM NaCl; 4.7 mM KCl; 3.0 mM $CaCl_2$; 1.2 mM $MgSO_4$; 25 mM $NaHCO_3$; 0.5 mM EDTA (free calcium, 2.5 mM). The perfusate contained 10 mM glucose during the initial non-recirculating perfusion.

Hearts and perfusion media were maintained at 37° C. Hearts were initially perfused for about 10 min without recirculation of the perfusate until a protocol was initiated. The recirculating volume of perfusate was 210 ml for the rat experiments, and 1000 ml for the rabbit experiments. Preliminary studies showed no significant change in the relative concentrations of substrates after 30 minutes of perfusion. The following $^{13}$C-enriched substrates were used: [3-$^{13}$C] lactate (99%, Isotec), [2,$^{13}$C] acetate (99%, MSD Isotopes), [1,2-$^{13}$C] acetate (99%, MSD Isotopes).

EXAMPLE 1

Isotopic NonSteady State and Metabolic Steady State

Hearts were switched to a recirculating system with the following unlabeled substrates: 0.25 mM acetate, 1.0 mM lactate and 10 mM glucose. After 20 min of recirculation, the perfusate was changed to one containing [1,2-$^{13}$C] acetate, [3-$^{13}$C] lactate, and glucose at the same concentrations. At the end of 30 min the heart was freeze clamped. Hearts in group 2 were treated identically to group 1 except that the perfusion period with labeled substrates was 5 min, followed by freeze clamping.

Figure 3A:
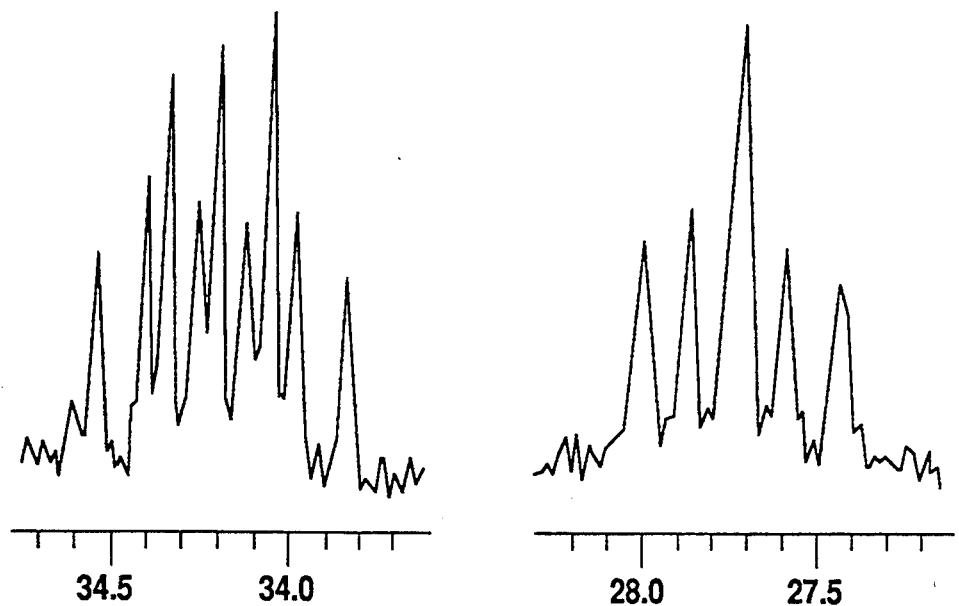
FIG. 3A shows proton decoupled $^{13}$C NMR spectra of the protonated carbons of glutamate from rat heart perfused for different periods with $^{13}$C-enriched substrate. The left side is the C4 resonance, and the right side is the C3 resonance. The spectrum is from a heart supplied for 30 min with [3-$^{13}$C] lactate, [1,2-$^{13}$C] acetate and unlabeled glucose.
Figure 3B:
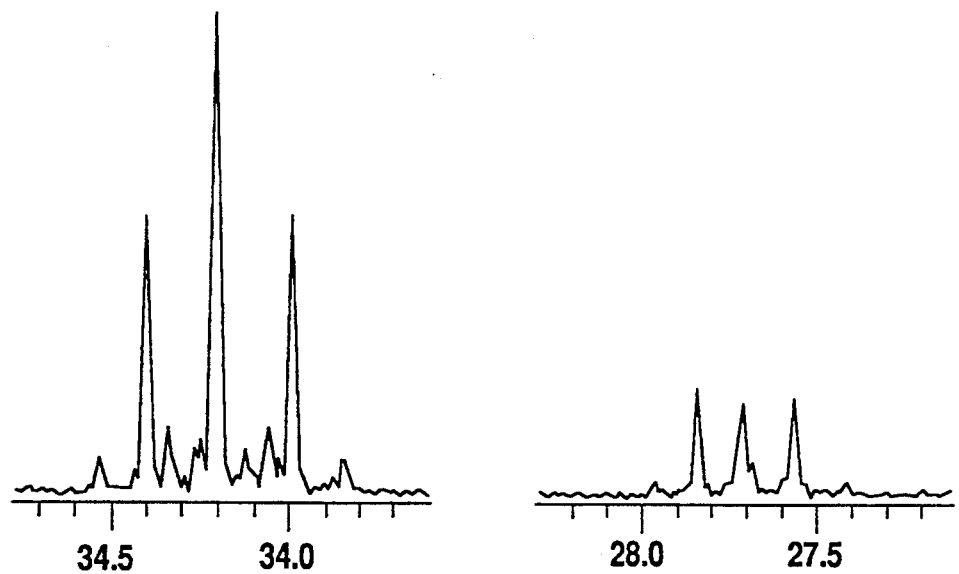
FIG. 3B shows proton decoupled $^{13}$C NMR spectra of the protonated carbons of glutamate from rat heart perfused for different periods with $^{13}$C-enriched substrates. The left side is the C4 resonance, and the right side is the C3 resonance. The spectrum is from a heart supplied for 5 min with same substrates. These spectra illustrate the results shown in Tables 2 and 3.

Proton decoupled $^{13}$C NMR spectra of extracts from hearts supplied for 5 or 30 min with [1,2-$^{13}$C] acetate, [3-$^{13}$C] lactate and glucose are shown in FIG. 3, and the multiplet measurements are summarized in Table 2.

TABLE 2

Influence of perfusion time on components of the glutamate multiplets in the $^{13}$C NMR spectra from hearts utilizing glucose, [$^{13}$C] lactate and [1,2-$^{13}$C] acetate. Data are the means ± standard deviations. C3S, C3D and C3T refer to the area of the singlet, doublet or triplet, respectively, in the 3 carbon resonance relative to the total area of that resonance. The variables describing the 4 carbon resonance are defined in the test.

| NMR Measurements | Perfusion Time | |
|---|---|---|
| | 5 min | 30 min |
| Carbon 3 | | |
| C3S | 0.35 ± 0.12 | 0.14 ± 0.04 |
| C3D | 0.57 ± 0.06 | 0.34 ± 0.06 |
| C3T | 0.08 ± 0.06 | 0.52 ± 0.10 |
| Carbon 4 | | |
| C4S | 0.31 ± 0.04 | 0.16 ± 0.02 |
| C4D34 | 0.07 ± 0.02 | 0.28 ± 0.02 |
| C4D45 | 0.52 ± 0.07 | 0.21 ± 0.03 |
| C4Q | 0.10 ± 0.02 | 0.35 ± 0.03 |
| C4/C3 | 4.48 ± 0.60 | 1.18 ± 0.09 |

Solution of equations 1 and 2 (applied to both groups of hearts) and the steady-state analysis (applied to hearts perfused for 30 min (22)) were used to measure the contribution of acetate, lactate and unlabeled sources to acetyl-CoA. The results are shown in Table 3 and show that the nonsteady-state and steady-state analyses yield the same results for hearts metabolizing labeled substrate for 30 min. The measured contributions of exogenous substrates to acetyl-CoA after 5 min of perfusion were also the same.

TABLE 3

Steady-state and nonsteady-state analysis of carbon flow into the citric acid cycle after brief (5 min) or prolonged (30 min) perfusion with labeled substrates. Data are means ± standard deviations.

| | Source of Acetyl-CoA | | |
|---|---|---|---|
| Perfusion time | unlabeled ($F_{c0}$) | lactate ($F_{c2}$) | acetate ($F_{c3}$) |
| 5 min (n = 3) | 0.28 ± 0.09 | 0.30 ± 0.07 | 0.42 ± 0.02 |
| 30 min (n = 4, non-steady-state analysis) | 0.24 ± 0.11 | 0.34 ± 0.05 | 0.42 ± 0.06 |
| 30 min (steady-state analysis) | 0.26 ± 0.09 | 0.32 ± 0.04 | 0.42 ± 0.05 |

EXAMPLE 2

Contribution of Exogenous Acetate to Normal and Post-ischemic Myocardium

Figure 4A:
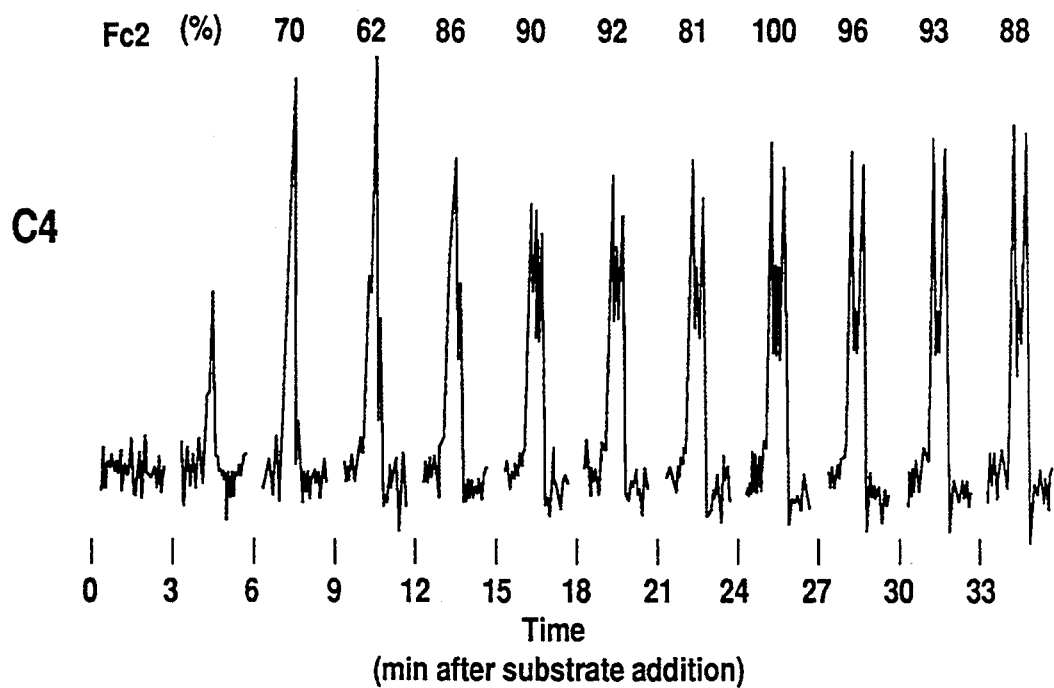
FIG. 4 shows the evolution of the $^{13}$C NMR spectrum in normal rat myocardium after addition of [2-$^{13}$C] acetate. The 4 carbon resonance (34.2 ppm, FIG. 4A) and the 3 carbon resonance (27.8 ppm, FIG. 4B) are shown. Each spectrum was acquired during the time shown on the abscissa after addition of 3.0 mM [2-$^{13}$C] acetate. The contribution of exogenous acetate to acetyl-CoA was calculated from each spectrum ($F_{c2}$).
Figure 4B:
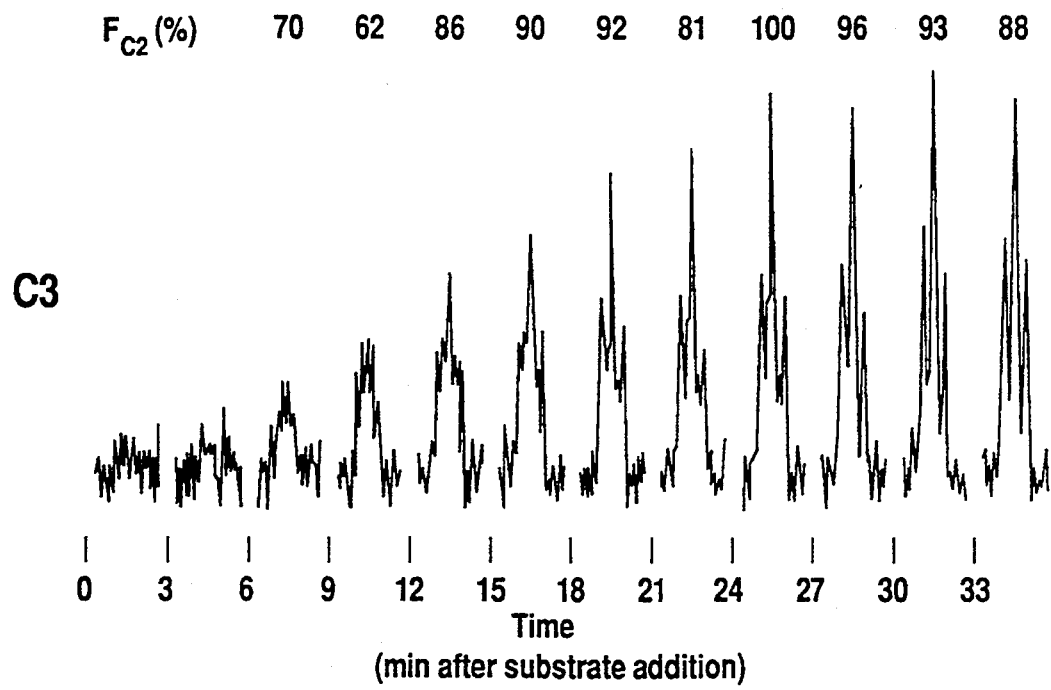
Figure 5A:
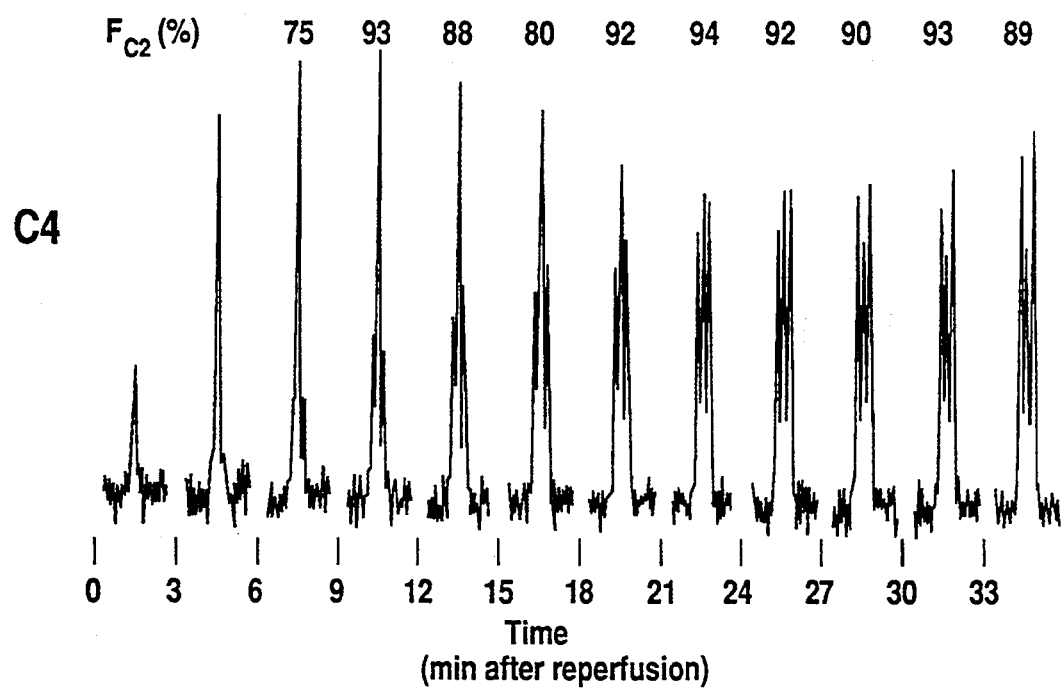
FIG. 5 shows the evolution of the $^{13}$C NMR spectrum in post ischemic rat myocardium after reperfusion and addition of [2$^{13}$C] acetate. The 4 carbon resonance (34.2 ppm, FIG. 5A) and the 3 carbon resonance (24.8 ppm, FIG. 5B) are shown. The contribution of exogenous acetate to acetyl-CoA was calculated from each spectrum ($F_{c2}$).
Figure 5B:
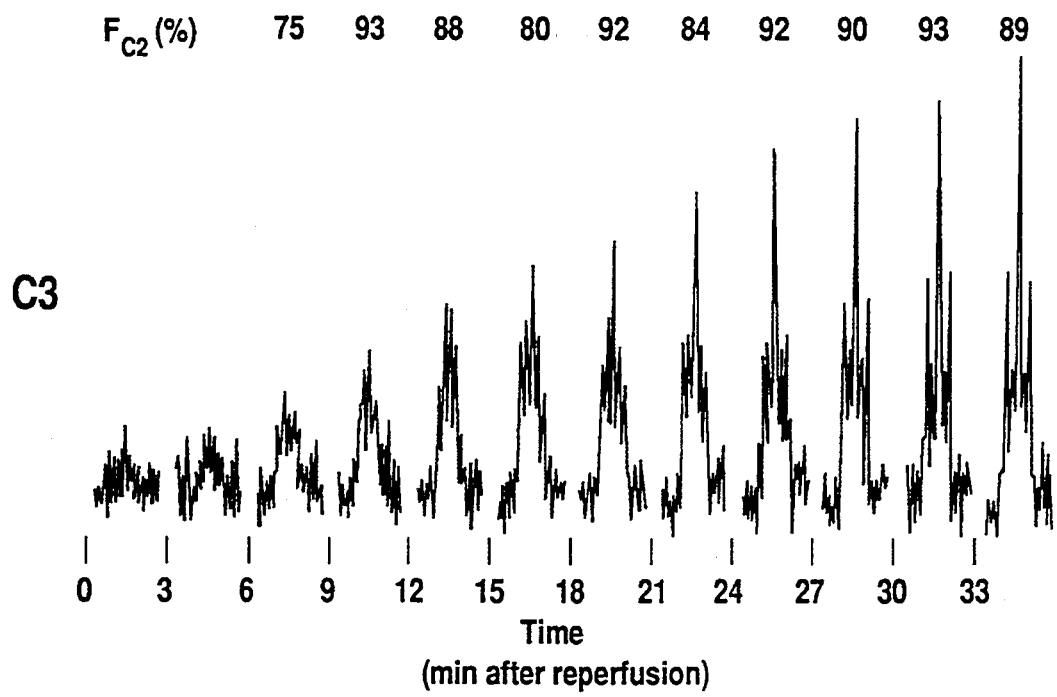

Hearts were studied directly in the NMR spectrometer; the substrates were 3 mM [2-$^{13}$C] acetate plus 10 mM glucose. After stable heart function was established in the magnet and perfusate was switched to 3 mM [2-$^{13}$C] acetate and 10 mM glucose, proton decoupled spectra were acquired every 3 min. Normoxic hearts (FIG. 4) rapidly incorporated $^{13}$C into glutamate and steadystate was reached in 20–25 min. The contribution of acetate to acetyl-CoA ($F_{c2}$) was measured after enrichment in carbon C3 was detected. Only equation 1 applies since [1,2-$^{13}$C] acetyl-CoA cannot be generated under these conditions and $F_{c3}=0$. The same procedure was repeated in the ischemic hearts, group 2, for 11 min, followed by reperfusion. As shown in FIG. 5, steadystate was not attained until after about 35 min. The steady-state isotopomer analysis of the final X3C NMR spectra showed that most of the acetyl-CoA was derived from exogenous acetate in both the normally perfused myocardium (0.95±0.3) and the reperfused myocardium (0.96±0.03).

EXAMPLE 3

Acetate and Lactate Utilization in Regional Ischemia

Rabbit hearts (groups 4 and 5, n=3) were used as a model of regional ischemia. The initial perfusate contained 10 mM glucose, 1.0 mM lactate and 0.5 mM acetate, and the hearts were allowed to stabilize for 15 min. Hearts in group 4 were switched to perfusate containing [1,2-$^{13}$C] acetate, [3-$^{13}$C] lactate, and glucose at the same concentrations; perfusion was continued for 30 min followed by freeze-clamping. Hearts that were freezeclamped were extracted in perchloric acid, neutralized with KOH, freeze-dried, and dissolved in $D_2O$ for NMR study. After stabilization, regional ischemia was produced in group 5 by occluding the left anterior descending coronary artery with an encircling suture for 30 min. Just prior to reperfusion methylene blue was added to the perfusate to stain the normally perfused myocardium. After reperfusion for 5 min, the perfusate was changed to one in which the unlabeled lactate and acetate were replaced by [1,2-$^{13}$C] acetate and [3-$^{13}$C] lactate in the same concentration; perfusion was continued for 7 min. Ischemic and normally perfused myocardium (identified visually by methylene blue stain) were freeze clamped. Typically, perfusion was preserved in the posterior septum, posterior wall and variable portions of the lateral wall.

Figure 6A:
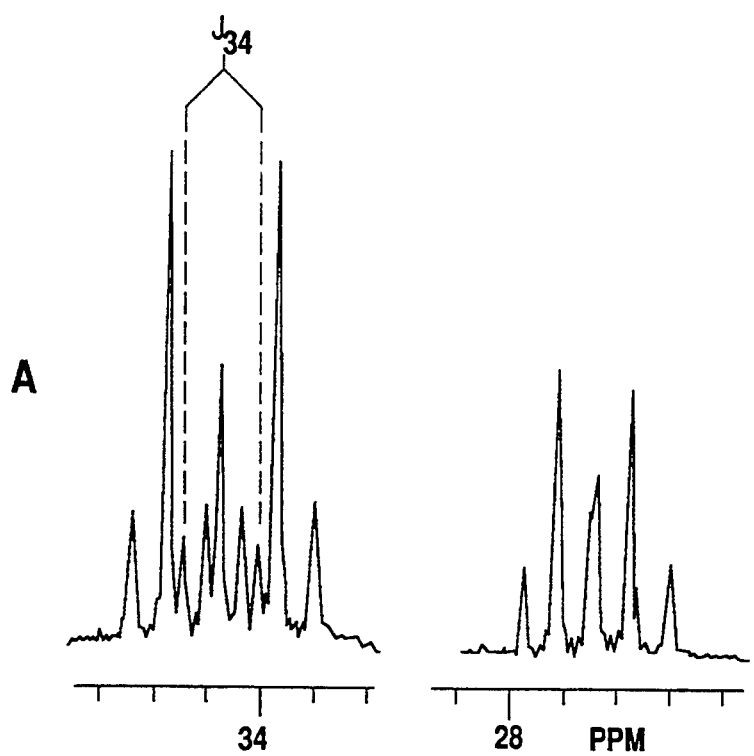
FIG. 6A shows proton decoupled $^{13}$C NMR spectra of tissue extracts from different regions of a single rabbit heart showing the glutamate C4 (left side) and C3 (right side) resonances. The substrates in the perfusate were [1,2-$^{13}$C] acetate, [3-$^{13}$C] lactate and glucose. The spectrum is acquired from normally perfused myocardiumo
Figure 6B:
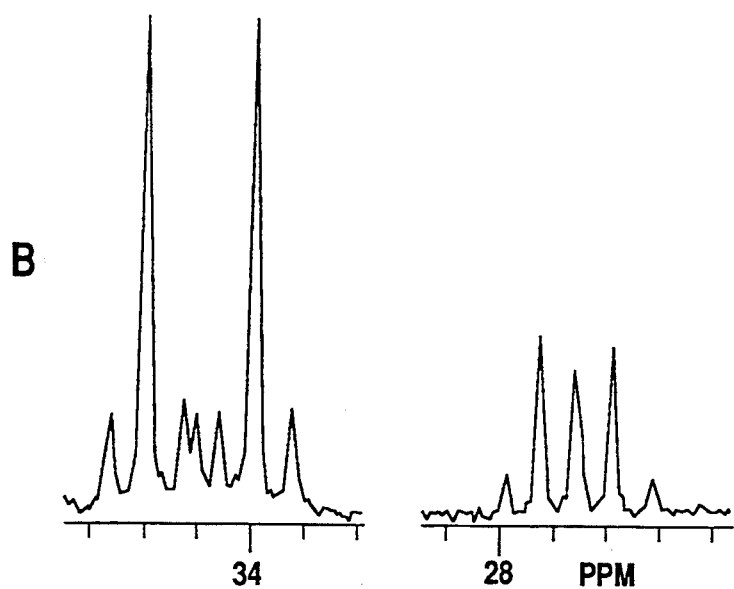
FIG. 6B shows proton decoupled $^{13}$C NMR spectra of tissue extracts from different regions of a single rabbit heart showing the glutamate C4 (left side) and C3 (right side) resonances. The substrates in the perfusate were [1,2-$^{13}$C] acetate, [3-$^{13}$C] lactate, and glucose. The spectrum is acquired from ischemic, reperfused myocardium.

In the normoxic myocardium (group 4), acetyl-CoA was derived from acetate (0.59±0.05), lactate (0.32±0.06) and unlabeled sources (0.09±0.02), either exogenous glucose or endogenous stores. In myocardium reperfused for 12 min (group 5), substrate utilization was highly variable. In the example shown in FIG. 6, acetyl-CoA in the normal myocardium was derived from acetate (48%, lactate (16%) and unlabeled sources (32%). In the same heart, acetyl-CoA in reperfused myocardium was derived from acetate (73%), lactate (9%) and unlabeled sources (18%).

PROPHETIC EXAMPLE 4

The present example outlines the procedure contemplated by the Applicant to be useful for the successful in vivo determination of substrate utilization in brain tissue.

Glucose Utilization in Brain

Any one of several labeling patterns in glucose could be used to determination glucose utilization. In a particular example, [U-$^{13}$C] glucose is used which metabolizes to [1,2-$^{13}$C] acetyl-CoA. The fraction of acetyl-CoA derived from administered glucose could be determined from $^{13}$C NMR spectra of the brain determined by NMR in vivo.

PROPHETIC EXAMPLE 5

The present example outlines the procedure contemplated by the Applicant to be useful for determination of fatty acid and glucose oxidation in skeletal muscle.

Fatty Acid and Glucose Oxidation in Skeletal Muscle

Skeletal muscle is capable of oxidizing both glucose and fatty acids, and the relative proportions are important for understanding many disease states, drug effects and other abnormal conditions. The patient or experimental animal is given (orally or intravenously) a mixture of [1-$^{13}$C] glucose and [U$^{13}$C] fatty acid such that adequate concentrations are established in the blood. The extremity of interest, for example the forearm or leg, is placed in an NMR spectrometer to obtain proton decoupled $^{13}$C spectra of the skeletal muscle. The fraction of acetyl-CoA derived from glucose (which in this instance would produce [1-$^{13}$C] acetyl-CoA), fatty acids (which would produce [1,2-$^{13}$C] acetyl-CoA, and unlabeled sources would then be determined as illustrated in Example 1. Alternatively, the muscle could be biopsied, extracted and analyzed as described.

PROPHETIC EXAMPLE 6

The present example outlines the procedure contemplated by the Applicant to be useful for determining fatty acid and amino acid utilization in the liver.

Fatty Acid and Amino ACid Utilization in the Liver

The metabolism of various compounds to acetyl-CoA represents the first steps of both biosynthetic and energy-producing pathways. A mixture of [U-x3C] fatty acids and [3-$^{13}$C] alanine could be supplied to the liver, and spectra could be obtained in vivo or on biopsy specimens.

The present invention has been described in terms of particular embodiments found by the inventors to comprise preferred modes of practice of the invention. It will be appreciated by those of skill in the art that in light of the present disclosure numerous modifications and changes can be made in the particular embodiments exemplified without departing from the intended scope of the invention. For example, non physiological substrates could be studied. All such modifications are intended to be included within the scope of the claims.

REFERENCES

The references listed below are incorporated herein by reference to the extent that they supplement, explain, provide a background for or teach methodology, techniques and/or compositions employed herein.

1. Williamson, J. R. and Krebs, H. A. Biochem. J. 80, 544–547 (1961).
2. Williamson, J. R. Biochem. J. 257, 1189–1195 (1962).
3. Neely, J. R., Denton, R. M., England, P. J., and Randle, P. J. Biochem. J. 128, 147–159 (1972).
4. Mickel, D. A. G., del Nido, P. J., Wilson, G. J., Harding, R. D., and Romaschin, A. D. Cardiovas. Res. 20, 256–263 (1986).
5. Myears, D. W., Sobel, B. E., and Bergmann, S. R. Am. J. Physiol. 253, H107–H114 (1987).
6. Liedke, J., DeMaison, L., Eggleston, A. M., Cohen, L. M. and Nellis, S. H. Circulation Research 62, 535–542 (1988).
7. Wyns, W., Schwaiger, M., Huang, S. C., Buxton, D. B., Hansen, H., Selin, C., Keen, R., Phelps, M. E., and Schelbert, H. R. Circ. Res. 65, 1787–1797 (1989).
8. Peuhkurinen, K. J. J. Mol. Cell. Cardiol. 16, 487–495 (1980).
9. Kornberg, H. L. Essays Biochem. 2, 1–31 (1966).
10. Chatzidakis, C. and Otto, D. A. Lipids 22, 620–626 (1987).
11. Veerkamp, J. M., van Moerkerk, H. T. B., Glatz, J. F. C., Zuurveld, J. G. E. M., Jacobs, A. E. M., Wagenmakers, A. J. M. Biochem. Med. Metab. Biol. 35, 248–259 (1986).
12. Lerch, R. A., Ambos, H. D., Bergmann, S. R., Welch, M. J., TerPogossian, M. M. and Sobel, B. E. Circulation 64, 689–699 (1981).
13. Schwaiger, M., Schelbert, H. R., Keen, R., Vinten-Johansen, J., Hansen, H., Selin, C., Barrio, J., Huang, S. C. and Phelps, M. E. J. Am. Coll. Cardiol. 6, 311–320 (1985).
14. Brown, M., Marshall, D. R., Sobel, B. E. and Bergmann, S. R. Circulation 76, 687–696 (1987).
15. London, R. E. Progress in NMR Spectroscopy 20, 337–383 (1988).
16. Walker, T. E., Han, C. H., Kollman, V. H., London, R. E. and Matwiyoff, N. A. J. Biol. Chem. 257, 1189–1195 (1982).
17. Chance, E. M., Seeholzer, S. H., Kobayashi, K., and Williamson, J. R. J. Biol. Chem. 258, 13785–13794 (1983).
18. Cohen, S. M. J. Biol. Chem. 258, 14294–14308 (1983).
19. Walker, T. E. and London, R. E. Appl. Environ. Microbiol. 53, 92–98 (1987).
20. Malloy, C. R., Sherry, A. D., and Jeffrey, F. M. H. J. Biol. Chem. 263, 6964–6971 (1988).
21. Sherry, A. D., Malloy, C. R., Roby, R. E., Rajogopal, A. and Jeffrey, F. M. H. Biochem. J. 254, 593–598 (1988).
22. Malloy, C. R. in Structural and Organizational Aspects of Metabolic Regulation, Alan R. Liss, Inc. (1990), pp. 363–374.
23. Moreland, C. G., and Carroll, F. I. J. Magn. Res. 15, 596–599 (1974).
24. LeCocq, C. and Lallemand, J. Y. J. Chem. Soc. Chem. Commun. 15–152 (1981).
25. Patt, S. L. and Shoolery, J. N. J. Magn. Res. 46, 487–495 (1982). Although the present invention has been described in some detail by way of illustration and example for purposes of clarity and understanding, it will be obvious that certain changes and modifications may be practiced within the scope of the claims.

What is claimed is:

1. A method of determining substrate utilization, comprising: preparing at least one $^{13}$C-carbon-labelled compound wherein the $^{13}$C labelled
    compound or a $^{13}$C labelled fragment of the compound enters the citric acid cycle;

subjecting a cell or tissue having an active citric acid cycle to the $^{13}$C-carbon-labelled compound; and measuring a carbon enrichment pattern in at least one citric acid cycle compound or a substance which preserves isotopic distribution in carbons 3, 4 and 5 of α-ketoglutarate to determine substrate utilization, said measuring being made prior to attaining metabolic or isotopic steady state.

2. The method of claim 1 wherein the $^{13}$C-labelled compound or fragment enters the citric acid cycle prior to metabolism to acetyl-CoA.

3. The method of claim 1 wherein the $^{13}$C-labelled compound or fragment is incorporated into acetyl-CoA.

4. The method of claim 1 wherein the $^{13}$C-labeled compound or fraqment is metabolized to acetyl-CoA.

5. The method of claim 1 wherein the $^{13}$C-labelled compound is a fatty acid.

6. The method of claim 1 wherein the $^{13}$-labeled compound is selected from a group consisting of acetate, propionate, butyrate, pentanoate, pentenoate, hexanoate, octanoate, decanoate, dodecanoate, tetradecanoate, hexadecanoate, octadecanoate, eicosanoate, palmitoleate, oleate, linoleate, linoleate, and arachidonate.

7. The method of claim 1 wherein the $^{13}$C-labeled compound is selected from a group consisting of lactate, pyruvate, glucose, fructose, acetoacetate, β-hydroxybutyrate, and ethanol.

8. The method of claim 1 wherein the $^{13}$C-labelled compound is an amino acid.

9. The method of claim 1 wherein the $^{13}$C-labelled compound is a carboxylic acid.

10. The method of claim 1 wherein the tissue is a body organ having citric acid cycle capacity.

11. The method of claim 1 wherein the tissue is selected from a group consisting of heart, brain, liver, lung, pancreas, white cells, lymphoid tissue, kidney and skeletal muscle.

12. The method of claim 1 wherein measuring enrichment of the pattern is by $^{13}$C NMR or $^{13}$C-edited NMR.

13. The method of claim 12 wherein the enrichment pattern is measured by $^{13}$C-edited NMR comprising $^{1}$H-NMR use of short and long range carbon proton coupling to measure isotopomer groups.

14. The method of claim 12 wherein the $^{13}$C-edited NMR is used to select each multiplet or singlet in a resonance.

15. The method of claim 1 wherein determining substrate utilization of one administered $^{13}$C-labelled compound metabolized to acetyl-CoA includes measuring $^{13}$C-NMR resonance areas of a multiplet of carbon C4 and a resonance area ratio of carbon C4 to C3, said carbons comprising a citric acid cycle component or a molecule exchanging with a citric acid cycle component that preserves isotopic distribution in carbons 3, 4 and 5 of α-ketoglutarate.

16. The method of claim 1 wherein determining substrate utilization of one administered $^{13}$C-labelled compound metabolized to acetyl-CoA includes measuring $^{13}$C-NMR resonance areas of a multiplet of carbon C4 and a resonance area ratio of carbon C4 to C3 or C5 to C3, said carbons comprising a citric acid cycle component or a molecule exchanging with a citric acid cycle component that preserves isotopic distribution in carbons 3, 4 and 5 of α-ketoglutarate.

17. The method of claim 1 wherein determining relative substrate utilization of two administered $^{13}$C-labelled compounds metabolized to acetyl-CoA and acetyl-CoA includes measuring $^{13}$C NMR resonance areas of two multiplets of carbon C4 and resonance area ratios of carbon C3 to C4 and C5 to C4 of a citric acid cycle component or a molecule exchanging with the citric acid cycle component that preserves isotopic distribution in carbons 3, 4 and 5 of α-ketoglutarate.

18. The method of claim 1 wherein determining relative substrate utilization of two administered $^{13}$C-labelled compounds metabolized to acetyl CoA and acetyl CoA includes measuring $^{13}$C NMR resonance areas of two multiplets of carbon C4 and resonance area ratios of C3 to C4 and C5 to C4 of a citric acid cycle component or exchanging molecule that preserves isotopic distribution of 3, 4 and 5 of α-ketoglutarate.

19. The method of claim 1 wherein determining relative substrate utilization of two administered $^{13}$C-labelled compounds metabolized to acetyl CoA and acetyl-CoA includes measuring $^{13}$C resonance areas of two multiplets of carbon C4 and resonance area ratios of carbon C3 to C4 of a citric acid cycle component or exchanging molecule that preserves isotopic distribution in carbons 3, 4 and 5 of α-ketoglutarate.

20. The method of claim 1 wherein determining relative substrate utilization of three administered $^{13}$C-labeled compounds metabolized to acetyl CoA, acetyl-CoA and acetyl-CoA includes measuring $^{13}$C NMR resonance areas of two multiplets of carbon C4, resonance area ratios of carbon C3 to carbon C4 and carbon C5 to C4 of a citric acid cycle component or an exchanging molecule that preserves isotopic distribution in carbons 3, 4 and 5 of α-ketoglutarate.

21. The method of claim 14, claim 15, claim 16, claim 17, claim 18, or claim 19 wherein the multipier or multiplets is a doublet, triplet, or quartet.

22. The method of claim 17 wherein said measurement further comprises correcting for effects of $^{13}$C-$^{13}$C dipolar interactions on $T_1$ and proton irradiation on intensities due to nuclear Overhauser enhancement.

23. The method of claim 1 wherein the citric acid cycle compound is a citrate derivative.

24. The method of claim 1 wherein the citric acid cycle compound is α-ketoglutarate, citrate, cis-aconitate or isocitrate.

25. The method of claim 1, wherein the $^{13}$C-labeled compound or fraqment is glutamine, glutamate, or γ-aminobutyric acid.

26. A method of assessing brain metabolic state, comprising the steps:

supplying $^{13}$C-labeled glucose to brain tissue;

performing a $^{13}$C NMR measurement on a brain tissue sample after exposure of the tissue to the $^{13}$C-labeled glucose, said measurement being performed prior to metabolic or isotopomeric steady-state;

determining a labeling pattern from $^{13}$C NMR measurements on a carbon C4/C3 ratio and a carbon C4 multiplet contribution from a citric acid cycle compound or a compound capable of exchanging $^{13}$C with the citric acid cycle compound; and determining from the labeling pattern the brain metabolic state.

27. A method of determining in vivo regional variations in tissue substrate utilization, comprising:

preparing at least one $^{13}$C carbon labeled compound wherein the labeled $^{13}$C compound or a $^{13}$C labeled fragment of the compound enters the citric acid cycle;

administering the $^{13}$C labeled compound or fragment;

performing a $^{13}C$ NMR measurement on the tissue after exposure of the tissue to the $^{13}C$ labeled compound, said measurement being performed prior to metabolic or isotopomeric steady-state; and determining enrichment of selected carbons from $^{13}C$ NMR measurements on $^{13}C$ carbons comprising a citric acid cycle compound or a substance which preserves isotopic distribution in carbons 3, 4 and 5 of α-ketoglutarate and determining therefrom regional tissue substrate variation.

28. The method of claim 27 wherein the tissue is diseased.

29. The method of claim 27 wherein the tissue is ischemic.

30. The method of claim 27 wherein the tissue is malignant.

* * * * *

UNITED STATES PATENT AND TRADEMARK OFFICE
CERTIFICATE OF CORRECTION

PATENT NO. : 5,413,917  
DATED : May 9, 1995  
INVENTOR(S) : Craig R. Malloy, et al Page 1 of 2

It is certified that error appears in the above-indentified patent and that said Letters Patent is hereby corrected as shown below:

In claim 16, column 15, line 59, after "metabolized to" insert --[1,2-$^{13}$C]--.

In claim 17, column 15, line 68, after "compounds metabolized to" insert --[2-$^{13}$C]--.

In claim 17, column 16, line 1, before "acetyl-CoA" insert --[1-$^{13}$C]--.

In claim 18, column 16, line 9, after "compounds metabolized to" insert --[1,2-$^{13}$C]--.

In claim 18, column 16, line 9, after "acetyl CoA and" insert --[1-$^{13}$C]--.

In claim 19, column 16, line 17, after "compounds metabolized to" insert --[2-$^{13}$C]--.

In claim 19, column 16, line 18, before "acetyl CoA" insert --[1,2-$^{13}$C]--.

In claim 20, column 16, line 25, after "compounds metabolized to" insert --[1-$^{13}$C]--.

In claim 20, column 16, line 25, after "acetyl CoA," insert --[2-$^{13}$C]--.

In claim 20, column 16, line 26, after "CoA and" insert --[1,2-$^{13}$C]--.

UNITED STATES PATENT AND TRADEMARK OFFICE
CERTIFICATE OF CORRECTION

PATENT NO. : 5,413,917
DATED : May 9, 1995
INVENTOR(S) : Craig R. Malloy, et al

It is certified that error appears in the above-indentified patent and that said Letters Patent is hereby corrected as shown below:

In claim 21, column 16, line 33, delete "multipier" and substitute --multiplet-- therefor.

In claim 25, column 16, line 45, delete "fraqment" and substitute --fragment-- therefor.

In claim 27, column 16, line 62, delete "vivo" and substitute --*vivo*-- therefor.

In claim 27, column 16, line 68, after "administering" insert --to a tissue--.

Signed and Sealed this

Nineteenth Day of September, 1995

Attest:

BRUCE LEHMAN

Attesting Officer

Commissioner of Patents and Trademarks